(12) United States Patent
St. Cyr et al.

(10) Patent No.: US 8,741,854 B2
(45) Date of Patent: Jun. 3, 2014

(54) COMPOSITIONS AND METHODS FOR FEEDING POULTRY

(75) Inventors: John A. St. Cyr, Coon Rapids, MN (US); Raj Khankari, Maple Grove, MN (US); Paul B. Addis, Cumberland, WI (US)

(73) Assignee: Bioenergy, Inc., Ham Lake, MN (US)

( * ) Notice: Subject to any disclaimer, the term of this patent is extended or adjusted under 35 U.S.C. 154(b) by 0 days.

(21) Appl. No.: 12/709,191

(22) Filed: Feb. 19, 2010
(Under 37 CFR 1.47)

(65) Prior Publication Data

US 2011/0021446 A1 Jan. 27, 2011

Related U.S. Application Data

(60) Provisional application No. 61/208,121, filed on Feb. 20, 2009.

(51) Int. Cl.
*A61K 31/70* (2006.01)

(52) U.S. Cl.
USPC .......................................................... 514/25

(58) Field of Classification Search
USPC .......................................................... 514/25
See application file for complete search history.

(56) References Cited

U.S. PATENT DOCUMENTS

| 6,251,442 B1 | 6/2001 | Aoyama et al. | |
| 2004/0087515 A1* | 5/2004 | Butler et al. | 514/25 |
| 2009/0297481 A1 | 12/2009 | Powlen | |

FOREIGN PATENT DOCUMENTS

| EP | 0661004 A1 | 7/1995 |
| JP | 06287136 | 10/1994 |
| WO | WO 96/22019 A1 * | 7/1996 |
| WO | 98/51164 | 11/1998 |
| WO | WO 00/56330 A1 | 9/2000 |
| WO | WO 2010/096689 A1 | 8/2010 |

OTHER PUBLICATIONS

USDA publication, Young chicken: Average liveweight at slaughter under Federal inspection, retrieved from the internet <http://usda.mannlib.cornell.edu/MannUsda/viewDocumentInfo.do?documentID=1367> on Dec. 7, 2011, 1 pages.*
Julian, Ascites in poultry, Avian Pathology, 1993, 22:3, 419-454.*
International Search Report and Written Opinion, issued May 20, 2010, Patent Application No. PCT/US2010/024788, filed Feb. 19, 2010, 10 pgs.
International Preliminary Report on Patentability, issued Aug. 23, 2011, Patent Application No. PCT/US2010/024788, filed Feb. 19, 2010, 7 pgs.
Omran et al., "Treatment Heart Failure: D-Ribose" *Pillie Willie*, Mar. 15, 2008. Retrieved from the Internet: <URL:http://cardiomyopathy-heart-failure.pilliewillie.nl/treament-heart-faiulure/treatment.cardiomyopathy.heart.failure.23.php>; 3 pgs.

* cited by examiner

*Primary Examiner* — Elli Peselev
(74) *Attorney, Agent, or Firm* — Mueting, Raasch & Gebhardt, P.A.

(57) ABSTRACT

Feed supplements for poultry raised using a rapid growth regimen are disclosed herein. The supplements include D-ribose in an amount effective to improve the resistance to cardiomyopathy in the poultry. Methods for feeding poultry are also disclosed herein.

17 Claims, 2 Drawing Sheets

| Treatment | Days | | | Description |
|---|---|---|---|---|
| | 0 - 35 | 0 - 43 | 0 - after final wts | |
| 1 | 10.2% | 16.4% | 27.6% | Negative Control |
| 2 | 5.3% | 12.0% | 15.1% | D-Ribose in drinking water |

COMPOSITIONS AND METHODS FOR FEEDING POULTRY

This application claims the benefit of U.S. Provisional Application Ser. No. 61/208,121, filed Feb. 20, 2009, which is herein incorporated by reference in its entirety.

BACKGROUND

In many parts of the world, chicken is a major source of animal protein in the human diet. A desirable source of chicken is broiler chicks, which are young, tender, small birds.

To meet the demand for chicken, broiler chicks are frequently raised using a rapid growth regimen such that the chicks attain market size in about six weeks. The regimen typically includes feeding the broiler chicks high nutrient feed that has been specially formulated for rapid growth. The regimen may also include exposure of the broiler chicks to continual or near continual light to encourage the chicks to feed longer each day. The regimen may further include exposure of the broiler chicks to relatively high temperatures, with optional periodic drops in temperature for cold stress conditioning.

Although rapid growth regimens can be effective in minimizing the time required for broiler chicks to attain the desired market weight, such rapid growth regimens can lead to problems. For example, although the broiler chicks have been selectively bred for rapid growth of the large breast tissue, other tissues and organs may not necessarily grow at the same rate, which can lead to problems such as bone structure and/or skeletal muscles being inadequate to support the weight of the growing chicks, which may ultimately lead to high morbidity (e.g., difficulty eating and sleeping) and early mortality levels (i.e., death occurring during the rapid growth regimen).

New compositions and methods that can improve the results attained from such rapid growth regimens are needed.

SUMMARY

In one aspect, the present disclosure provides a method for reducing early mortality in poultry (e.g., chickens, ducks, geese, turkeys, and combinations thereof). In certain embodiments, the method improves the resistance to cardiomyopathy in the poultry. In certain embodiments, at least a portion of the high morbidity and early mortality levels observed for broiler chicks raised using high growth regimens are attributable to a weakening of the heart muscle or a change in heart muscle structure (i.e., cardiomyopathy), which encompasses issues such as ascites and sudden death syndrome.

In one embodiment, the method includes: feeding the poultry a diet including high nutrient feed; and supplementing the diet with D-ribose. As used herein, the term "supplementing" as applied to D-ribose is intended to refer to intentionally adding D-ribose to the diet, in addition D-ribose, if any, that may naturally occur in the diet formulation (e.g., in the high nutrient feed). In certain embodiments, the high nutrient feed includes one or more of shelled corn, roasted soy beans, alfalfa, fish or meat meal, vitamin and mineral supplement, aragonite, hard rock particles, coccidiostat, and combinations thereof. In preferred embodiments, the dosage of the D-ribose is effective to reduce the incidence of ascites and/or sudden death syndrome in poultry such as broiler chicks. In certain embodiments, the dosage of the D-ribose is 50 to 500 mg/kg body weight per day. In certain preferred embodiments, the dosage of the D-ribose is 100 to 300 mg/kg body weight per day. In other preferred embodiments, the dosage of the D-ribose is 150 to 250 mg/kg body weight per day. In other certain preferred embodiments, the dosage of the D-ribose is 200 mg/kg body weight per day. The recited dosages can be individual daily dosages or average daily dosages over a period of days or weeks.

Typically, the poultry is fed ad libitum, and the D-ribose supplementation of the diet occurs for at least a week, and in preferred embodiments for at least two weeks. In some embodiments, the poultry is fed ad libitum, and the D-ribose supplementation of the diet occurs during one or more portions of the growth period. For example, the D-ribose supplementation can occur during a first portion of the growth period and/or a last portion of the growth period, each portion of which can independently be, for example, one or more weeks. In other preferred embodiments, the poultry is fed ad libitum, and the D-ribose supplementation of the diet occurs throughout the course of a rapid growth regimen.

In another aspect, the present disclosure provides a method of feeding poultry (e.g., chickens, ducks, geese, turkeys, and combinations thereof). In one embodiment, the method includes administering an aqueous solution of D-ribose to the poultry. In certain embodiments, the dosage of the D-ribose is 50 to 500 mg/kg body weight per day. In certain preferred embodiments the dosage of the D-ribose is 100 to 300 mg/kg body weight per day. In other preferred embodiments, the dosage of the D-ribose is 150 to 250 mg/kg body weight per day. In other certain preferred embodiments, the dosage of the D-ribose is 200 mg/kg body weight per day. The recited dosages can be individual daily dosages or average daily dosages over a period of days or weeks.

In even another aspect, the present disclosure provides a feed supplement for poultry raised using a rapid growth regimen. The supplement includes D-ribose in an amount effective to improve resistance to cardiomyopathy in the poultry. In certain embodiments the poultry include broiler chicks.

In certain embodiments, the methods and supplements disclosed herein may be particularly advantageous at higher altitudes (e.g., at least 3000 feet above sea level, in some embodiments at least 4000 feet above sea level, and in certain embodiments at least 5000 feet above sea level).

DEFINITIONS

The terms "comprises" and variations thereof do not have a limiting meaning where these terms appear in the description and claims.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

DETAILED DESCRIPTION OF ILLUSTRATIVE EMBODIMENTS

Figure 1:
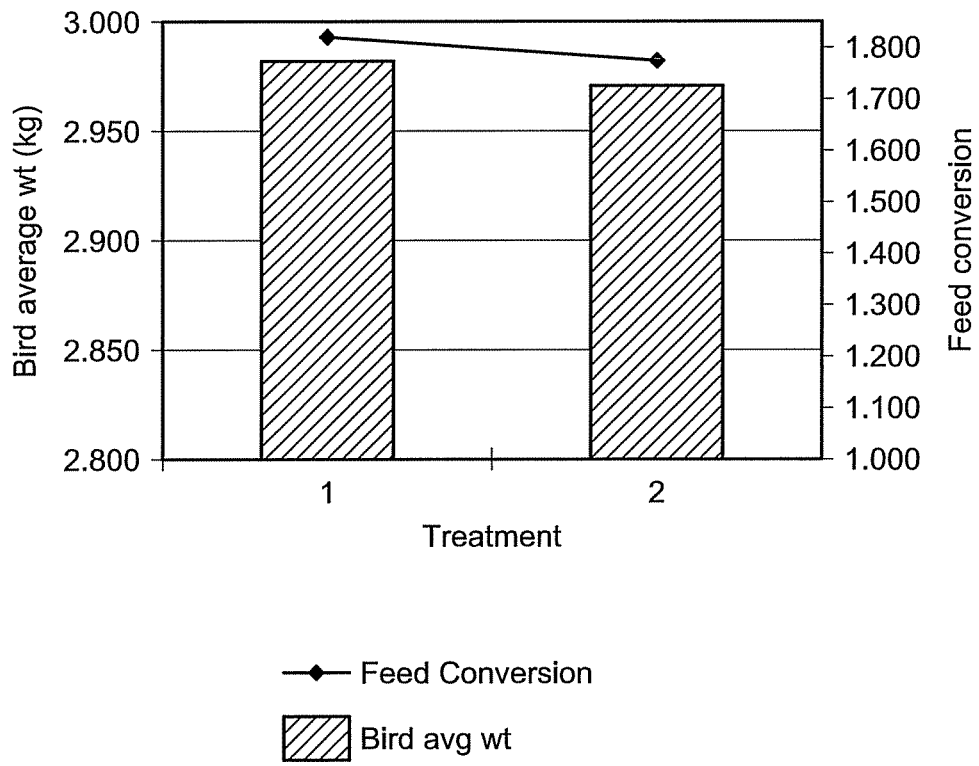
FIG. 1 shows the average weight and feed conversion of broiler chicks supplemented with D-ribose compared to controls not supplemented.

Supplementing the diet of poultry (e.g., broiler chicks) with D-ribose can lead to reduced levels of early mortality in the poultry. In some embodiments, supplementing the diet of the poultry with D-ribose can be effective for improving resistance to cardiomyopathy in poultry. For example, in certain embodiments, supplementing the diet of broiler chicks with D-ribose resulted in reduced cardiomyopathic incidences for the broiler chicks raised using a rapid growth regimen. In certain embodiments, reductions in morbidity and/or early mortality levels are observed, which can be attributed to a reduction in cardiomyopathic incidences such as ascites and sudden death syndrome.

In one aspect, the present disclosure provides a method of feeding poultry (e.g., chickens, ducks, geese, turkeys, and combinations thereof). In preferred embodiments, the poultry includes chickens, and in certain preferred embodiments, broiler chicks. The method of feeding poultry includes supplementing the poultry diet with D-ribose. In certain embodiments, the D-ribose can be supplemented, for example, in solid form or in an aqueous solution.

For example, in one embodiment, the method includes administering an aqueous solution of D-ribose to the poultry. In certain embodiments, the dosage of the D-ribose is 50 to 500 mg/kg body weight per day. In certain preferred embodiments the dosage of the D-ribose is 100 to 300 mg/kg body weight per day. In other preferred embodiments, the dosage of the D-ribose is 150 to 250 mg/kg body weight per day. In other certain preferred embodiments, the dosage of the D-ribose is 200 mg/kg body weight per day. The recited dosages can be individual daily dosages or average daily dosages over a period of days or weeks.

In another aspect, the present disclosure provides a method for improving resistance to cardiomyopathy in poultry (e.g., broiler chicks). The method includes: feeding the poultry a diet including high nutrient feed; and supplementing the diet with D-ribose. In certain embodiments, the high nutrient feed includes one or more of shelled corn, roasted soy beans, alfalfa, fish or meat meal, vitamin and mineral supplement, aragonite, hard rock particles, coccidiostat, and combinations thereof. In preferred embodiments, the dosage of the D-ribose is effective to reduce the incidence of ascites and/or sudden death syndrome in the poultry. In certain embodiments, the dosage of the D-ribose is 50 to 500 mg/kg body weight per day. In certain preferred embodiments, the dosage of the D-ribose is 100 to 300 mg/kg body weight per day. In other preferred embodiments, the dosage of the D-ribose is 150 to 250 mg/kg body weight per day. In other certain preferred embodiments, the dosage of the D-ribose is 200 mg/kg body weight per day. The recited dosages can be individual daily dosages or average daily dosages over a period of days or weeks.

Typically, the poultry is fed ad libitum, and the D-ribose supplementation of the diet occurs for at least a week, and in preferred embodiments for at least two weeks. In some embodiments, the poultry is fed ad libitum, and the D-ribose supplementation of the diet occurs during one or more portions of the growth period. For example, the D-ribose supplementation can occur during a first portion of the growth period and/or a last portion of the growth period, each portion of which can independently be, for example, one or more weeks. In other preferred embodiments, the poultry is fed ad libitum, and the D-ribose supplementation of the diet occurs throughout the course of a rapid growth regimen.

In even another aspect, the present disclosure provides a feed supplement for poultry raised using a rapid growth regimen. The supplement includes D-ribose in an amount effective to improve the resistance to cardiomyopathy in the poultry. In certain embodiments the poultry include broiler chicks.

The present invention is illustrated by the following examples. It is to be understood that the particular examples, materials, amounts, and procedures are to be interpreted broadly in accordance with the scope and spirit of the invention as set forth herein.

EXAMPLES

Five hundred and ten male chicks of a commercial breed, "Cobb 500", were purchased from a commercial hatchery. At receipt, the age was approximately one day. The birds were divided into test and control groups of 255 each and housed in 30 pens. Birds were housed in concrete mini-floor pens (four feet by four feet) in an environmentally controlled facility at approximately 5200 feet elevation above sea level. All birds were placed in pens containing clean litter. Environmental conditions for the birds, (i.e. floor space, bird density, temperature, lighting, feeder and water space) were similar for all groups. In order to prevent bird migration, each pen was checked to assure that no openings greater than one inch existed for approximately 12 inches in height between pens. Environmental conditions simulated commercial field conditions. From days 1 to 4, the lights were on 24 hours per day; from days 5 to 43, the lights were turned off for one hour per day. Light intensity was 1.0 to 1.3 foot candles.

Birds were vaccinated for Mareks at the hatchery and vaccinated on receipt at the research facility for Newcastle-Infectious Bronchitis (Fort Dodge Animal Health, Fort Dodge, Iowa) via a spray cabinet. No other vaccinations or treatments were administered during the study.

Treatments were assigned to the pens using a completely randomized block design. Two extra birds were placed in each pen to allow for culls and starve-outs. On day 7, any extra birds remaining were removed, leaving 15 birds in each pen.

The starter crumbled feed (days 0 to 20), grower pellet feed (days 20 to 35) and finisher pellet feed (days 35 to 43) were standard broiler diets manufactured at the research facility and stored in bulk, mash form. Final diet mixing, pelleting and crumbling were conducted at the research facility. Both test and control groups were fed the same diet ad libitum from one hanging 17-inch diameter tubed feeder per pen beginning day 5. A chick feeder tray was placed in each pen for the first four days. Feed added and removed from the pens from day zero to day 43 was weighed and recorded. A typical high nutrient diet formulation is summarized in Table I.

TABLE I

| Ingredient | % Composition w/w |
|---|---|
| Shelled corn | 40-60 |
| Roasted soy beans | 25-35 |
| Alfalfa | 4-7 |
| Fish or meat meal | 5-8 |
| Poultry Nutribalance (vitamin and mineral supplement) | ~3 |
| Aragonite (Calcium salt) | ~2 |
| Grit (any hard rock particles) | ad libitum |
| Salinomycin (coccidiostat) | ~.05 |

The source of calcium should be a calcium salt that does not readily dissolve in the gut; oyster shell is not a suitable calcium supplement. Free range chickens pick up enough grit from foraging to aid in digestion, while chickens held in cages must be provided with grit. The amount can vary and is not significant.

Water was provided ad libitum throughout the study via one bell drinker in each pen. Drinkers were checked twice daily to assure a constant and clean water supply to the birds.

Water treatment for the test group was mixed daily in one large volume and led into the bell drinker from a five gallon bucket container. It was apparent that algae or bacterial growth in the five gallon bucket containers for the test group may have significantly decreased the volume and quality of drinking water to the test group at times during the study. Water for the control group was provided from normal water lines in the research facility.

D-ribose was added daily to the drinking water of the test group at a concentration calculated to be about 200 mg/kg body weight/day.

The test facility pens and birds were observed at least twice daily for general flock condition, lighting, water, feed, ventilation and anticipated events. The minimum and maximum temperature of the test facility was recorded once daily. Starting on day 0, any bird that was found dead or dying was removed and sacrificed, weighed and necropsied. Cull birds that were unable to reach feed or water were sacrificed, weighed and documented. The weight and probable cause of death and necropsy findings were recorded. Birds were weighed on days 35 and 43.

Average bird weight on each weigh day was summarized. The average feed conversion was calculated using the total feed consumption in a pen divided by the total weight of surviving birds and weight of birds that died or were removed from the pen.

Figure 2:
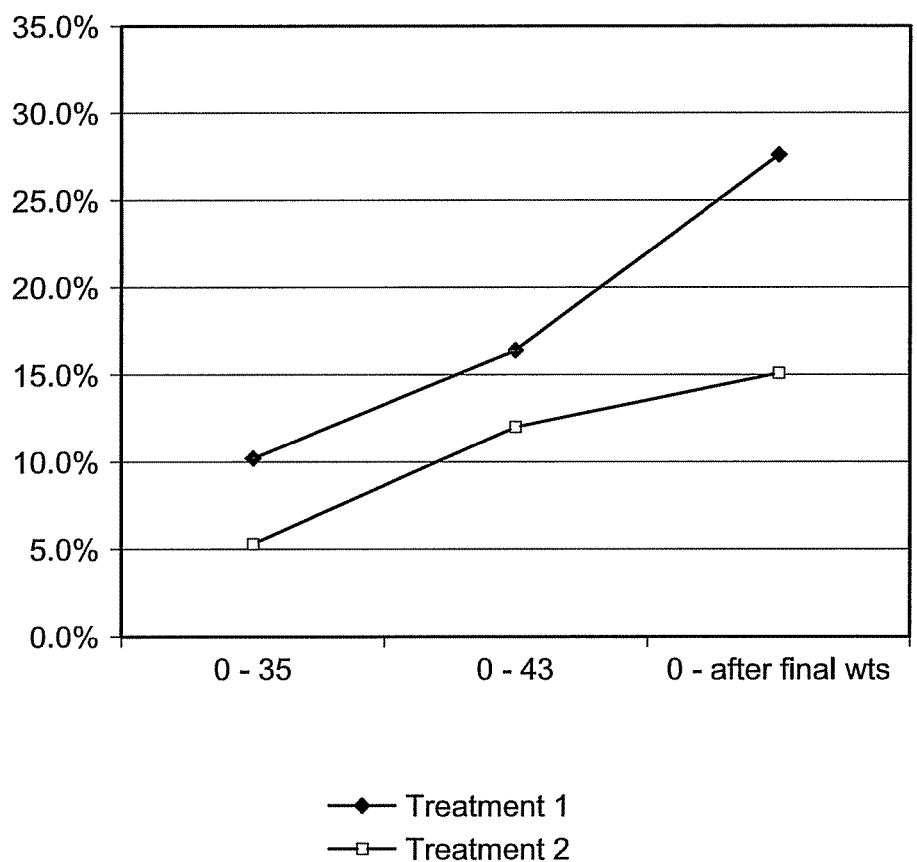
FIG. 2 shows the summary of cardiomyopathic incidences of broiler chicks supplemented with D-ribose compared to controls not supplemented.

The birds were challenged to simulate worst case field conditions. Growth was maximized by feeding a high nutrient commercial diet (top 25% Agri-Stats). An aggressive lighting system was used to increase the feeding time each day. On nights 3 and 4, from about 16:00 to 7:00, the birds were chilled to a temperature of less than 80° F. As can be seen in FIG. 1, the trend for the groups' weights and feed conversion were slightly better in the control group, but the differences were not statistically significant. The most significant finding can be seen in FIG. 2, which shows sharply reduced cardiomyopathic incidences in the test group. D-ribose supplementation decreased observed cardiomyopathic incidences from 27.6% to 15.1% in this challenged environment.

It is possible that the performance (weight gain and feed conversion) may have been even better in the test group if the algae and/or bacterial bloom (slime development) in the five gallon water containers had been avoided. The algae or bacterial over growth clogged water lines at times (thus decreasing water available to the birds in that pen) and obviously decreased the quality of the water available to those birds.

While the details of poultry early mortality are not fully known, the hearts are observed to be enlarged-dilated, edematous, with biventricular failure. This type of spontaneous cardiomyopathy with sudden death syndrome has been termed "round heart disease." Ascites is present, which is seen in right-sided heart failure. It is posited that the stress during this enforced fast growth regimen, centering on growth of the skeletal muscles, outpaces the cardiac growth, leading to cardiac collapse with a high mortality and some recovery. Once past this enforced growth period, the poultry will show declining mortality rates from cardiomyopathic incidences; mortality peaks at two weeks, with most deaths occurring by four weeks.

The only significant difference between the control and the ribose group noted was the decrease in observed cardiomyopathic incidences, indicating that ribose did not substantially interfere with the programmed enforced rapid growth.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for reducing early mortality in broiler chicks, the method comprising:
   feeding the broiler chicks a diet consisting of water, D-ribose in a pharmaceutically effective amount to reduce early mortality in broiler chicks, and a feed consisting of one or more ingredients selected from the group consisting of shelled corn, roasted soy beans, alfalfa, fish meal, meat meal, a vitamin supplement, a mineral supplement, a calcium salt, grit, and a coccidiostat.

2. The method of claim 1 wherein the method improves the resistance to cardiomyopathy in the broiler chicks.

3. The method of claim 2 wherein the dosage of the D-ribose is effective to reduce the incidence of ascites in the broiler chicks; to reduce the incidence of sudden death syndrome in the broiler chicks; or to reduce the incidence of both ascites and sudden death syndrome in the broiler chicks.

4. The method of claim 3 wherein the dosage of the D-ribose is 50 to 500 mg/kg body weight per day.

5. The method of claim 4 wherein the dosage of the D-ribose is 100 to 300 mg/kg body weight per day.

6. The method of claim 5 wherein the dosage of the D-ribose is 150 to 250 mg/kg body weight per day.

7. The method of claim 6 wherein the dosage of the D-ribose is 200 mg/kg body weight per day.

8. The method of claim 4 wherein the broiler chicks are fed ad libitum, and the D-ribose supplementation of the diet occurs for at least a week.

9. The method of claim 8 wherein the broiler chicks are fed ad libitum, and the D-ribose supplementation of the diet occurs for at least two weeks.

10. The method of claim 9 wherein the broiler chicks are fed ad libitum, and the D-ribose supplementation of the diet occurs throughout the course of about six weeks.

11. The method of claim 1 wherein the broiler chicks are fed and supplemented at an altitude of at least 3000 feet above sea level.

12. A method of feeding broiler chicks, the method comprising administering an aqueous solution consisting of water and D-ribose in a pharmaceutically effective amount to reduce early mortality in broiler chicks to the broiler chicks, wherein the method reduces early mortality in the broiler chicks.

13. The method of claim 12 wherein the dosage of the D-ribose is 50 to 500 mg/kg body weight per day.

14. The method of claim 13 wherein the dosage of the D-ribose is 100 to 300 mg/kg body weight per day.

15. The method of claim 14 wherein the dosage of the D-ribose is 150 to 250 mg/kg body weight per day.

16. The method of claim 15 wherein the dosage of the D-ribose is 200 mg/kg body weight per day.

17. A method for reducing early mortality in broiler chicks, the method comprising:
   feeding the broiler chicks a diet consisting of water and a feed consisting of one or more ingredients selected from the group consisting of shelled corn, roasted soy beans, alfalfa, fish meal, meat meal, a vitamin supplement, a mineral supplement, a calcium salt, grit, and a coccidiostat; and supplementing the diet with a composition consisting essentially of D-ribose in a pharmaceutically effective amount to reduce early mortality in broiler chicks.

* * * * *